US00PP35109P2

(12) United States Plant Patent
Ronald

(10) Patent No.: US PP35,109 P2
(45) Date of Patent: Apr. 18, 2023

(54) ***MALUS* PLANT NAMED 'JEFWALL'**

(50) Latin Name: ***Malus* hybrid**
Varietal Denomination: Jefwall

(71) Applicant: Jeffries Nurseries Ltd, Portage la Prairie (CA)

(72) Inventor: Wilbert Ronald, Portage la Prairie (CA)

(73) Assignee: JEFFRIES NURSERIES LTD, Portage la Prairie (CA)

( * ) Notice: Subject to any disclaimer, the term of this patent is extended or adjusted under 35 U.S.C. 154(b) by 0 days.

(21) Appl. No.: 17/724,676

(22) Filed: Apr. 20, 2022

Related U.S. Application Data

(60) Provisional application No. 63/181,950, filed on Apr. 29, 2021.

(51) Int. Cl.
*A01H 5/02* (2018.01)

(52) U.S. Cl.
USPC ..... Plt./173

(58) Field of Classification Search
USPC ..... Plt./173, 175
CPC ... A01H 5/02; A01H 5/08; A01H 5/00; A01H 6/74; A01H 6/7418
See application file for complete search history.

(56) References Cited

PUBLICATIONS

Issuu Jeffries Nurseries 2017 Northern Garden Introductions, retrieved on Aug. 4, 2022 at https://issuu.com/psrpsr/docs/jnlintros, cover page and p. 16. (Year: 2017).*

* cited by examiner

*Primary Examiner* — June Hwu
(74) *Attorney, Agent, or Firm* — Penny J Aguirre

(57) ABSTRACT

A new and distinctive cultivar of flowering crabapple, botanically known as *Malus* 'Jefwall', that is characterized by its narrow columnar plant habit, its glossy foliage that is green in color, and its flower buds that are pink in color and flowers that are white in color.

2 Drawing Sheets

Botanical classification: *Malus* hybrid.
Variety denomination: 'Jefwall'.

BACKGROUND OF THE INVENTION

The present invention relates to a new and distinct cultivar of *Malus* of hybrid origin and will be referred to hereafter by its cultivar name, 'Jefwall'. 'Jefwall' is a deciduous tree grown for use as an ornamental landscape plant.

The new *Malus* arose from a breeding program conducted by the Inventor at a nursery in Portage la Prairie, Manitoba, Canada. The objective of the breeding program was to develop a new cultivar of *Malus* with a columnar plant habit, disease resistance, glossy green foliage, and reduced fruit size.

The new *Malus* originated from a cross made in 2008 between *Malus* 'Jefspire' (not patented) as the female parent and *Malus* 'Spring Snow' (not patented) as the male parent. 'Jefwall' was selected as a unique single plant derived from the resulting seedlings of the above cross in 2011.

Asexual propagation of the new cultivar was first accomplished by vegetative budding in August of 2010 under the direction of the Inventor in Portage la Prairie, Manitoba, Canada. Asexual propagation by vegetative budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Jefwall' as a unique cultivar of *Malus*.

1. 'Jefwall' exhibits a narrow columnar plant habit.
2. 'Jefwall' exhibits glossy foliage that is green in color.
3. 'Jefwall' exhibits flower buds that are pink in color and flowers that are white in color.
4. 'Jefwall' exhibits cold hardiness at least to U.S.D.A Zone 2.

The female parent of 'Jefwall' differs from 'Jefwall' in having foliage that is bronze-green in color until late summer, fruit that is much larger in size, and sparse flowering habit. The male parent of 'Jefwall', differs from 'Jefwall' in having a round plant habit and in being sterile. 'Jefwall' can also be compared to the cultivars 'Jeflite' (not patented) and 'JFS KW214MX' (U.S. Plant Pat. No. 31,076). 'Jeflite' is similar to 'Jefwall' in having a glossy green foliage and spring flowers that are white in color. 'Jeflite' differs from 'Jefwall' in having fruit that is smaller in size, a more floriferous blooming habit, and in lacking a columnar plant habit. 'JFS KW214MX' is similar to 'Jefwall' in having a columnar habit and spring flowers that are white in color. 'JFS KW214MX' differs from 'Jefwall' in producing a heavier fruit load and in being less winter hardy (U.S.D.A Zone 4).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to listings on websites by ISSUU, Jeffries Nurseries, Eagle Lake Nurseries, Broderick Gardens, Landscape Trades, NVK Nurseries, Falk Nurseries, and Sherwood Forests.

BRIEF DESCRIPTION OF THE DRAWINGS

The accompanying color photographs illustrate the overall appearance and distinct characteristics of the new *Malus* as grown in Portage la Prairie, Manitoba, Canada. The plant in the photograph is about 4.5 years in age with 'Jefwall' budded onto *Malus* rootstock.

The photograph in FIG. 1 provides a view of the narrow columnar plant habit of 'Jefwall'.

Figure 1:
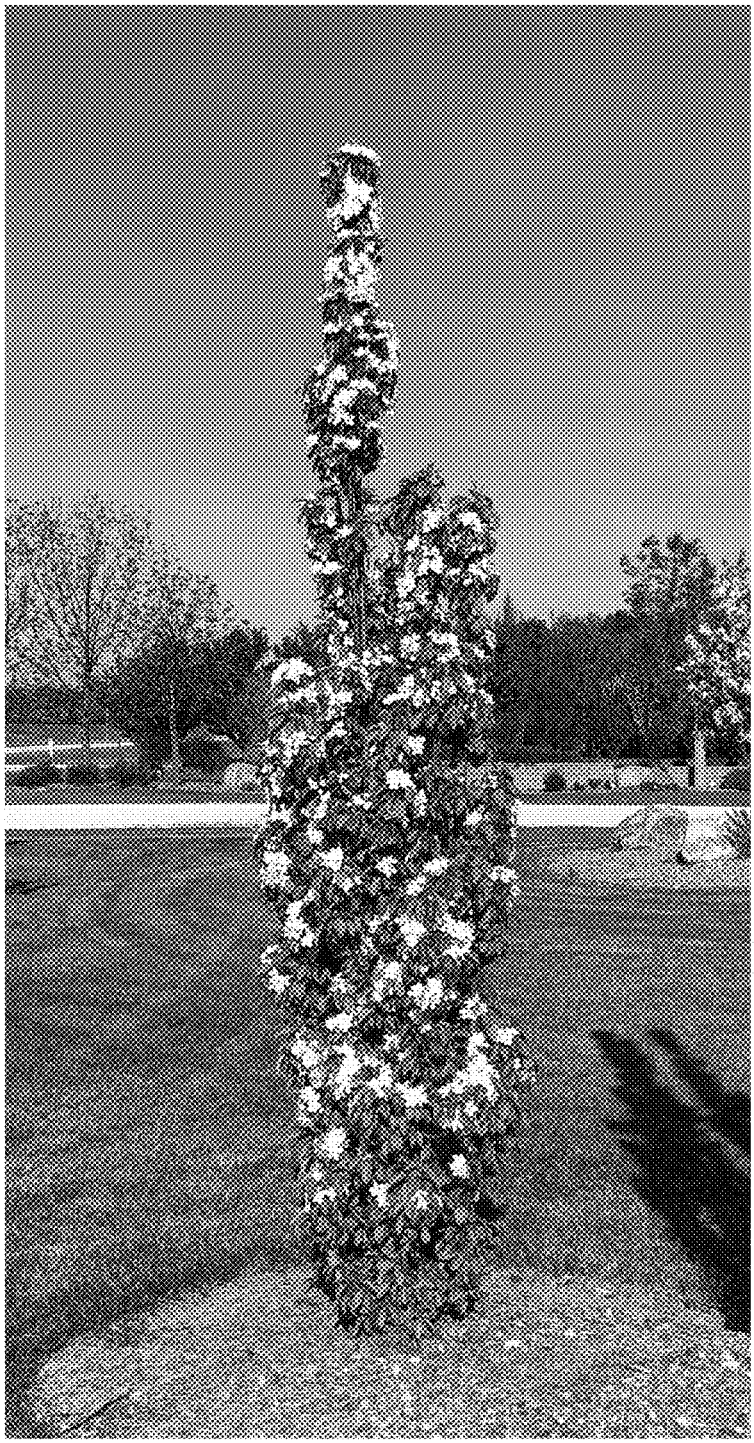
Figure 2:
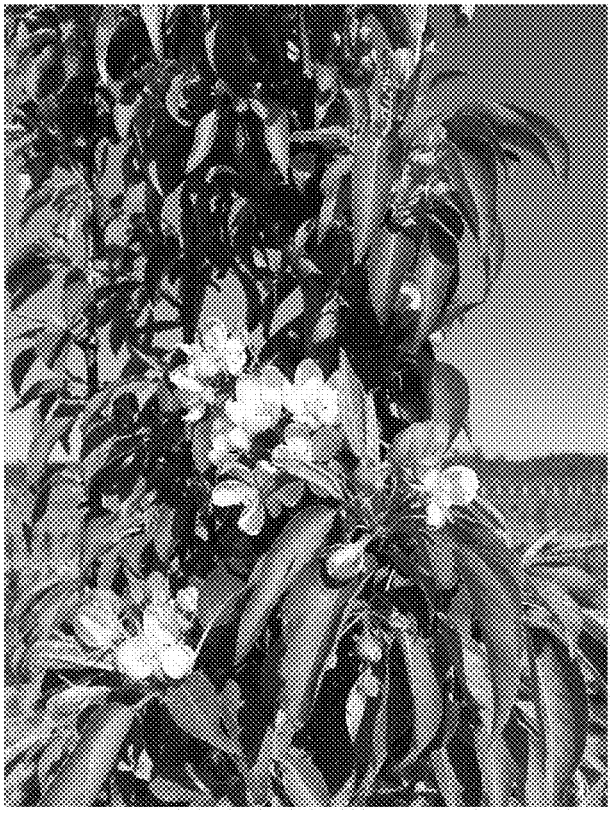

The photograph in FIG. 2 provides a close-up view of the flowers of 'Jefwall'.

Figure 3:
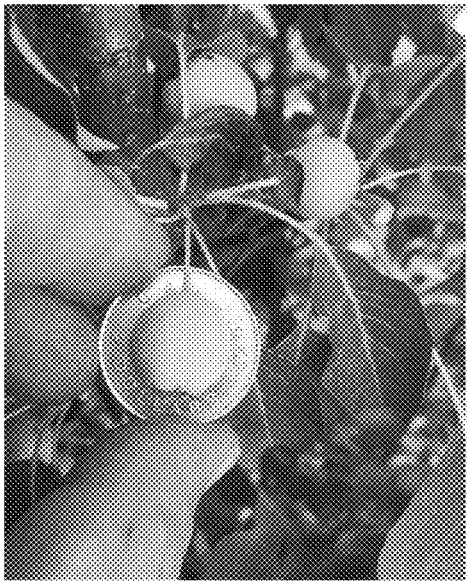

The photograph in FIG. 3 provides a close-up view of the fruit of 'Jefwall'.

The colors in the photographs may differ slightly from the color values cited in the detailed botanical description, which accurately describe the colors of the new *Malus*.

DETAILED BOTANICAL DESCRIPTION

The following is a detailed description of four-year-old trees of 'Jefwall' budded onto *Malus* rootstock and grown in a trial plot in Portage la Prairie, Manitoba, Canada. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period.*—2 weeks in mid to late May.

*Plant type.*—Deciduous tree.

*Tree habit.*—Narrowly columnar.

*Height and spread.*—Average of 6 m in height and 1.8 m in diameter in the landscape as a 4-year-old tree.

*Diseases and pests.*—Good resistance to apple scab (caused by *Venturia inaequalis*) and fireblight (caused by *Erwinia amylovora*), no viruses found to date, and no resistance or susceptibility to pests has been observed.

*Cold Hardiness.*—At least in U.S.D.A. Zone 2.

*Propagation*—Budding onto *Malus* rootstock, rootstock used will vary depending on propagation zonation, Dolgo is often used.

*Root development.*—About 3 weeks to bud onto rootstock and about 5 months to finish a young plant.

*Growth rate.*—Vigorous.

Branches:

*Branching habit.*—1 vertical main branch, 6 secondary stems, strong, upright branches held at an angle of about 70° to the main stem.

*Branch internode length.*—2.5 cm.

*Branch shape.*—Round.

*Branch strength.*—Strong.

*Branch size.*—An average of 90 cm in length and 1.5 cm in width, 2 year growth 27 cm, trunk 2 cm in diameter.

*Branch surface.*—New emerging growth; densely covered with woolly pubescence 145C in color, younger stems and mature stems; smooth, glossy and moderately covered with oval lenticels and average of 15 per sq cm, 0.5 mm in diameter, 161A in color, older bark; bark is a blend of N199B and 199A in color with lenticels; about 20 per 7 sq cm, 161A in color, about 0.5 mm in width.

Leaf orientation: Horizontal.

*Leaf division.*—Simple.

*Leaf shape.*—Elliptic.

*Leaf size.*—Average of 11 cm in length and 7 cm in width.

*Leaf apex.*—Acuminate.

*Leaf base.*—Cuneate to oblique.

*Leaf surface.*—Emerging and young leaves densely covered with woolly hairs 161B in color on both surfaces, mature leaves very sparsely covered with short stiff hairs, NN155C in color, 0.3 mm in length on both surfaces with upper leaf surface medium glossiness and lower leaf surface dull.

*Leaf margin.*—Serrate.

*Leaf internode length.*—Average of 2 cm.

*Leaf color.*—Emerging; upper and lower surface 146B, young upper surface; between 144A and 143A, young lower surface; N148A, mature upper surface; 147A, no anthocyanin present, mature lower surface; 147B, fall; upper surface 163B, lower surface 163C.

*Leaf venation.*—Pinnate, upper surface 144B, lower surface 145C.

*Petioles.*—Average of 5 cm in length and 2 mm in diameter, 145C, upper surface flushed with 178B in color, sides of petiole are very densely covered with woolly hairs 137A in color.

*Stipules.*—200A in color, an average of 1 cm in length and 2 mm in width, matte surfaces.

Flower description:

*Lastingness of flowers.*—About 10 days.

*Number of flowers.*—Average of 5 per corymb.

*Inflorescence type.*—Corymb of rotate flowers.

*Inflorescence size* (*corymb*).—An average of 7 cm in length and 11 cm in width.

*Flower buds.*—55A in color prior to opening, round in shape, average of 1.8 cm in length and 1 cm in diameter.

*Flower size.*—Average of 5 cm in diameter and 3 cm in depth.

*Flower quantity.*—Average of 5 per axillary node.

*Flower fragrance.*—Medium.

*Flower aspect.*—Outward.

*Flower shape.*—Flat.

*Petals.*—5 per flower, un-fused, not overlapping, obovate in shape, obtuse apex, round base, entire margin, average of 2.5 cm in length and 1.5 cm in width, color upper and lower surface when opening: a blend of 55A and N999D, color upper and lower surface when mature: N999D, upper and lower surface is smooth and satiny.

*Sepals.*—5 per flower, 142A in color on upper and lower surface, pubescent surface, triangular in shape, entire margins, acuminate apex, base fused into tube, average of 2 cm in length and 5 mm in width with tube portion 5 mm in length and width.

*Pedicel.*—143A in color, average of 4 cm in length and 2.5 mm in width, surface is pubescent.

*Pistil.*—Compound carpel, stigmas; 3 fused at base, 1 cm in length, style; 149A in color, stigma; minute, ovary; pubescent, 149A in color.

*Stamens.*—Average of 16 per flower, anther; oblong in shape, 160B in color, filament; 1.5 cm in length and 155D in color, pollen; moderate in quantity and 4B in color.

Fruit and seed description:

*Shape.*—Round.

*Size.*—Average of 1.25 cm in diameter.

*Skin.*—At maturity; smooth surface with a glaucous coating, depending on degree of ripeness color a blend of 42A, 33B and 53A.

*Fruit calyx.*—Not present.

*Fruit stalk size.*—An average of 4 cm in length and 1 mm in diameter.

*Flesh color.*—158B.

*Fruit presence.*—First visible in June in Manitoba, Canada, retained through winter.

*Seed.*—Nearly renal-shaped, 4 to 5 per fruit, 1 per chamber, 5 mm in length and 2 mm in width, 170B in color.

It is claimed:

1. A new and distinct cultivar of *Malus* tree named 'Jefwall' as herein illustrated and described.

* * * * *